United States Patent [19]

Mazo et al.

[11] Patent Number: 6,005,069

[45] Date of Patent: *Dec. 21, 1999

[54] PRODUCTION OF POLYSUCCINIMIDE AND DERIVATIVES THEREOF IN A SULFUR-CONTAINING SOLVENT

[75] Inventors: Grigory Ya. Mazo; Jacob Mazo, both of Skokie, Ill.

[73] Assignee: Donlar Corporation, Bedford Park, Ill.

[ * ] Notice: This patent is subject to a terminal disclaimer.

[21] Appl. No.: 08/768,996

[22] Filed: Dec. 18, 1996

[51] Int. Cl.$^6$ ............................. C08G 69/10; C08G 73/10
[52] U.S. Cl. ........................... 528/363; 528/328; 528/361; 528/373; 525/418; 525/420; 548/520; 548/545
[58] Field of Search ...................................... 528/373, 328, 528/363, 361; 548/520, 545; 525/420, 418

[56] References Cited

U.S. PATENT DOCUMENTS

| | | | |
|---|---|---|---|
| 5,057,597 | 10/1991 | Koskan | 528/328 |
| 5,219,952 | 6/1993 | Koskan et al. | 525/419 |
| 5,221,733 | 6/1993 | Koskan et al. | 528/363 |
| 5,296,578 | 3/1994 | Koskan et al. | 528/363 |
| 5,315,010 | 5/1994 | Koskan et al. | 548/520 |
| 5,371,177 | 12/1994 | Paik et al. | 528/361 |
| 5,371,179 | 12/1994 | Paik et al. | 528/363 |
| 5,466,779 | 11/1995 | Ross | 528/363 |
| 5,484,945 | 1/1996 | Nagatomo et al. | 548/520 |
| 5,491,213 | 2/1996 | Batzel | 528/480 |
| 5,508,434 | 4/1996 | Batzel et al. | 548/520 |
| 5,756,595 | 5/1998 | Mazo et al. | 525/420 |

*Primary Examiner*—P. Hampton-Hightower
*Attorney, Agent, or Firm*—Olson & Hierl, Ltd.

[57] ABSTRACT

Polysuccinimide of varying molecular weight has been prepared in a solvent system by heat polymerization of aspartic acid. The solvent system includes a sulfur oxygen acid and a sulfur oxygen acid salt. In a preferred embodiment, aspartic acid is polymerized in a liquid solvent reaction mixture at a temperature in the range of about 110° C. to about 320° C.

22 Claims, No Drawings

PRODUCTION OF POLYSUCCINIMIDE AND DERIVATIVES THEREOF IN A SULFUR-CONTAINING SOLVENT

FIELD OF THE INVENTION

This invention relates to the production of polysuccinimide and derivatives thereof by solution polymerization of aspartic acid at an elevated temperature.

BACKGROUND OF THE INVENTION

Polyanhydroaspartic acid (also known as polysuccinimide) is the key commercial precursor to polyaspartic acid, an increasingly important biodegradable water soluble polymer. The chemistry and process fundamentals of polysuccinimide by the thermal condensation polymerization of aspartic acid are well established in the patent and journal literature. Illustrations are described in U.S. Pat. No. 5,057,597, to Koskan and U.S. Pat. No. 5,315,010 and No. 5,221,733 to Koskan et al. The weight average molecular weights obtained by thermal condensation of aspartic acid by these methods are usually about 5000.

No commercial processes employing phosphoric acid based additives to prepare relatively low weight average molecular weight polysuccinimide exist for several reasons. First, the cost of the reactants, phosphoric acid and its anhydride, are relatively high. Second, waste streams containing phosphate salts are damaging to the environment because phosphorous promotes algae blooms in lakes and rivers which in turn deplete the level of oxygen necessary to sustain marine life.

Commonly owned U.S. Pat. No. 5,508,434 to Batzel et al. describes an unstirrable, highly viscous, thin layer melt process for the production of polysuccinimide with the concomitant release of water vapor. However, this particular process requires post-synthetic treatment of the product which adds to the overall cost of production. The post-synthetic treatment includes the additional steps of collecting and crushing the porous solid succinimide then extracting the sulfuric acid and salts contained within by numerous washing steps followed by drying of the product.

The present invention provides an economical, ecologically tolerable, and phosphoric acid free solvent system manufacturing process for preparing relatively low weight average molecular weight polysuccinimide in the range of about 1000 to 5000 Mw.

SUMMARY OF THE INVENTION

A method of preparing polysuccinimide by the solution polymerization of aspartic acid in a solvent system which also acts as the catalyst is disclosed. The solvent system is constituted by a sulfur oxygen acid and a sulfur oxygen acid salt. The present method overcomes problems associated with prior art phosphoric acid methods of making polysuccinimide and also provides an economical and ecologically acceptable process.

The solvent system preferably comprises at least one sulfur oxygen acid in combination with at least one salt thereof having a counterion derived from an inorganic or organic base. Sulfur oxygen acids useful for present purposes include sulfuric acid, fuming sulfuric acid, sulfamic acid, polysulfuric acid, sulfonic acids such as methanesulfonic acid and mixtures thereof, and inorganic as well as organic salts and mixtures thereof. Preferred sulfur oxygen acid salts include an inorganic salt such as an alkali metal salt, an alkaline earth metal salt, a transition metal salt, and mixtures thereof. Preferred organic salts include a sulfate salt such as urea sulfate, pyridinium sulfate, pyridinium bisulfate, ammonium sulfate, and mixtures thereof. A quaternary ammonium sulfate is also suitable. A particularly preferred quaternary ammonium salt is tetramethylammonium sulfate.

The solution polymerization can be carried out at a temperature above about 110° C. by employing a stirred reactor under ambient air, inert gas or vacuum. Various types of solution agitation may be employed to increase the reaction rate and enhance the removal of water, such as the use of falling film evaporators, wiped film evaporators and sparging-agitated reactors. A preferred temperature range is about 110° C. to about 320° C., and a more preferred range is about 130° C. to about 300° C. Particularly preferred is a reaction temperature of about 185° C.

DETAILED DESCRIPTION OF THE INVENTION

The present inventive solution polymerization process produces polysuccinimide having weight average molecular weight (MW) below about 5,000 with relatively high conversion.

In practicing the method aspects of this invention, the weight average molecular weight, particle size, polydispersity, and color of the resulting polysuccinimide can be controlled by varying the molar ratios of the reactants, the temperature of the reaction, the reactor system, and the reaction time. If desired, the polysuccinimide produced by the inventive method can be hydrolyzed to polyaspartic acid.

As presently practiced and preferred, the reaction mixture employed during the polymerization is a stirrable, liquid medium. The reaction mixture initially contains aspartic acid dissolved in a sulfur-containing solvent. A sulfur oxygen acid in combination with at least one salt thereof having a counterion derived from an inorganic or organic base is a preferred solvent for aspartic acid. The molar ratio of sulfur oxygen acid to aspartic acid preferably is at least about 2, and more preferably is in the range of about 2.5 to about 5. A molar ratio of about 4 is particularly preferred. The molar ratio of sulfur oxygen acid:sulfur oxygen acid salt in the solvent is preferably in the range of about 1:1 to about 1:1.5. The molar ratio of sulfur oxygen acid-sulfur oxygen acid salt solution to aspartic acid preferably is about 3:1.

Presently preferred sulfur oxygen acids include the aforementioned sulfuric acid, fuming sulfuric acid, sulfamic acid, polysulfuric acid, sulfonic acids such as methanesulfonic acid and toluenesulfonic acid and salts thereof. If desired, the salt of the sulfur oxygen acid can be prepared in situ by adding the appropriate amount of an inorganic base, such as sodium hydroxide, potassium hydroxide or an organic base such as pyridine or ammonia to an amount of the sulfur oxygen acid. The salt is soluble in the sulfur oxygen acid when the acid-salt combination is heated to polymerization temperatures. Particularly preferred inorganic salts of sulfuric acid are sodium sulfate, potassium sulfate and mixtures thereof. Preferred organic salts include a sulfate salt such as urea sulfate, pyridinium sulfate, pyridinium bisulfate, ammonium sulfate, and mixtures thereof. Particularly preferred are the quaternary ammonium sulfates, such as tetramethylammonium sulfate.

Solution polymerization can be carried out in a conventional stirred reactor at polymerization temperatures that preferably are in the range of about 110° C. to about 320° C., more preferably in the range of about 130° C. to about 300° C. A solution temperature of about 185° C. is particularly preferred. Solution polymerization advantageously proceeds rapidly over a time period in the range of about 5 minutes to 4 hours, preferably of about 1 to 3 hours in cases where simple stirred reactor vessels open to the atmosphere are used. The reaction can be carried out under an atmosphere of ambient air, inert gas such as nitrogen, or vacuum. Various types of solution agitation may be employed to increase the reaction rate and enhance the removal of water, such as the use of falling film evaporators, wiped film evaporators and sparging-agitated reactors.

In one preferred solution polymerization embodiment, a solvent mixture is prepared first. Next, this solvent mixture is heated with stirring, to form a substantially homogeneous solution. Aspartic acid is combined with the hot solution to form a liquid reaction mixture. The hot solution is at a preselected reaction temperature sufficient to initiate solution polymerization of aspartic acid to polysuccinimide. The polymerization temperature is maintained while the reaction mixture is agitated to produce polysuccinimide. Preferably agitation is continued until the polymerization is substantially complete.

In another preferred solution polymerization embodiment, a liquid reaction mixture is prepared by first forming a mixture of sulfur oxygen acid and aspartic acid which is then charged into a stirred reactor vessel. The temperature of the foregoing mixture is then raised to a temperature sufficient to dissolve the aspartic acid, but below the preselected polymerization temperature. Then, at least two salts of the sulfur oxygen acid are added to and dissolved in the hot solution. The temperature of the resulting solution is then further raised to a preselected polymerization temperature and maintained at about that temperature in the stirred reactor vessel until polysuccinimide is produced.

As presently practiced and preferred, the polysuccinimide produced by solution polymerization can be isolated and recovered by cooling the reaction mixture to about ambient temperature, then adding it to water in an amount sufficient to precipitate the polysuccinimide product. As an option, the polysuccinimide product may be filtered and washed with a water-miscible non-solvent for polysuccinimide, preferably acetone. Finally, the polysuccinimide product is dried, preferably at a temperature of about 110° C., and preferably under reduced pressure of about −70 kPa for about 3 hours. The polysuccinimide product usually has a MW in the range of about 1,000 to about 5,000.

Without wishing to be bound by any theory, it is believed that the sulfur oxygen acid and salt system, preferably a sulfur oxygen acid and mixed salt system, acts as both solvent for the reactants as well as catalyst for the polymerization of aspartic acid to polysuccinimide.

The solution polymerization as presently practiced proceeds more rapidly than a thin layer polymerization process. The produced polysuccinimide is more readily recoverable from solutions or suspensions than from foamed or expanded melts resulting from a thin layer method of polymerization.

The present solution polymerization process can be carried out by employing conventional reactors which are relatively inexpensive, commonly available, and allow relatively high production rates in relatively small plant areas. In contradistinction, thin layer reactors require a larger plant space which may not always be available.

The polysuccinimide produced in accordance with the methods of the present invention can be used per se, or can be combined with an aqueous basic solution of ammonium hydroxide, sodium hydroxide, sodium carbonate, and the like, to produce salts of polyaspartic acid by hydrolysis. Base hydrolysis of polysuccinimide to polyaspartic acid can be carried out under a wide variety of conditions, but preferably is effected at a pH value of at least about 8 and higher, and at a temperature of about 100° C. Acid hydrolysis of the polysuccinimide product is also possible.

The following Examples further illustrate the invention.

EXAMPLES 1–6

Preparation of Polysuccinimide by Solution Polymerization of Aspartic Acid In A Sulfuric Acid-Ammonium Sulfate System In Examples 1–6 the following general method was employed. Mixtures of concentrated sulfuric acid (98% w/w, about 62.46–65.3 g, 0.612–0.627 mol) and ammonium sulfate (99% w/w, about 115.19–117.55 g, 0.863–0.881 mol) were separately prepared by first premixing the starting materials together in flasks in the relative amounts shown in Table 1, below. Each mixture was then charged individually into separate reactor flasks with stirring. The flasks were each placed into a hot oil bath at a preselected setpoint temperature of about 215° C. The temperature of the contents of each flask was increased to either about 180° C. (Examples 4–6) or about 195° C. (Examples 1–3), forming a liquid solution.

Next, aspartic acid (98.5%, 30 grams, 0.222 mol) was added over a period of several minutes to each solution. The selected reaction temperature was maintained with stirring for a time period of about 1 to 3 hours as indicated in Table 1. During this time period, aspartic acid dissolved in the reaction mixture. After the time periods had expired, the contents of each flask were poured into a tray for ease of handling and allowed to cool to room temperature.

Next, cool water (about 1 liter) was added to the crude product, mixed, then filtered. The recovered solids were washed with acetone (about 200 ml) and dried in an oven set at a temperature of about 110° C. with reduced pressure of about −70 kPa for about 3 hours. Each one of the resulting products was a finely divided white powder that was confirmed as being polysuccinimide by Infrared Spectroscopy (IR) and Nuclear Magnetic Resonance (NMR) analysis. The molecular weight of the polysuccinimide produced was determined by conversion of the polysuccinimide to sodium polyaspartate followed by size exclusion chromatography (SEC) analysis. The % purity was determined by titration for free aspartic acid, then subtracting this value from 100%. The % conversion to polysuccinimide product was determined by weighing the final product.

TABLE 1

Examples of Sulfuric Acid and Ammonium Sulfate Systems

| Ex. | Asp (g) | H₂SO₄ (g)I | (NH₄)₂SO₄ (g)II | Molar Ratio Asp:I:II | Time (h) | Temp (° C.) | Mw; Mn | % Pure | % Conversion |
|---|---|---|---|---|---|---|---|---|---|
| 1 | 30 | 62.46 | 117.55 | 1:2.75:3.97 | 1 | 195 | 1615;988 | 95 | 53 |
| 2 | 30 | 62.46 | 117.55 | 1:2.75:3.97 | 2 | 195 | 2156;1209 | 97 | 95 |
| 3 | 30 | 62.46 | 117.55 | 1:2.75:3.97 | 3 | 195 | 2294;1214 | 97 | 89 |
| 4 | 30 | 64.06 | 115.19 | 1:2.82:3.88 | 1 | 180 | 2456;1314 | 97 | 70 |
| 5 | 30 | 64.06 | 115.19 | 1:2.82:3.88 | 2 | 180 | 2492;1250 | 97 | 91 |
| 6 | 30 | 64.06 | 115.19 | 1:2.82:3.88 | 3 | 180 | 2546;1361 | 99 | 96 |

As shown by the data in Table 1, polysuccinimide of relatively high purity was produced having a MW in the range of about 1,600 to about 2,600. The conversion to polysuccinimide was also relatively high.

EXAMPLES 7–9

Preparation of Polysuccinimide by Solution Polymerization of Aspartic Acid In A Sulfuric Acid-Mixed Sulfate System In Examples 7–9 the general method employed in Examples 1–6 was followed except that, as indicated in Table 2 below, the preformed mixture for Example 7 contained concentrated sulfuric acid (98% w/w, about 58.68 g, 0.575 mol), ammonium sulfate (99% w/w, about 95.56 g, 0.716 mol) and potassium sulfate (99%, about 25.82 g, about 0.147 mol) and the preformed mixtures for Examples 8–9 contained concentrated sulfuric acid (98% w/w, about 73.46 g, 0.719 mol), potassium sulfate (99%, about 58.79 g, 0.334 mol) and sodium sulfate (99%, about 52.24 g, about 0.385 mol). The temperature either was about 185° C. (Examples 7–8) or about 200° C. (Example 9), and was maintained in each reaction mixture for a time period of about 1 to about 2 hours as indicated in Table 2.

During this time period, aspartic acid was observed to fully dissolve in each solution. After the preselected time periods had expired, the general procedure for isolating and characterizing the reaction product as described for Examples 1–4 was followed for each of Examples 7–9.

Each one of the dried products was a finely divided white powder that was confirmed as polysuccinimide by previously described methods. The purity and conversion to polysuccinimide were determined as previously described.

EXAMPLE 10

Preparation of Polysuccinimide by Solution Polymerization of Aspartic Acid In A Sulfuric Acid-Mixed Sulfate System This Example illustrates a solution polymerization embodiment in which aspartic acid was first dissolved in sulfuric acid and then a combination of mixed sulfate salts was added to the acid solution.

A solvent was prepared by mixing concentrated sulfuric acid (98% w/w, about 75.68 g, 0.742 mol) and aspartic acid (98.5%, 30.02 g, 0.222 mol) in a flask. The solution was then charged into a vessel and was immersed in a hot oil bath set at a preselected setpoint temperature of about 190° C. and stirred. As the contents of the flask approached a temperature of about 160° C., the aspartic acid dissolved. Upon the solution reaching the foregoing temperature, potassium sulfate (99%, about 22.21 g, about 0.126 mol) and ammonium sulfate (99%, 82.18 g, 0.616 mol) were added to the solution. This reaction mixture contained a molar ratio of aspartic acid:sulfuric acid:potassium sulfate:ammonium sulfate of about 1:3.34:0.57:2.77.

The temperature of the resulting solution was then raised to about 180° C. and maintained for a time period of about 2 hours. After the preselected time period had expired, the general procedure for isolating, drying and characterizing the reaction product as described for Examples 1–4 was followed.

The product was a finely divided light tan powder that was confirmed as being about 97% pure polysuccinimide by IR analysis. The conversion to polysuccinimide was determined to be about 81%. The polysuccinimide was characterized as having a MW of about 2,949 and a Mn of about 1,609 by SEC analysis.

TABLE 2

Examples of Sulfuric Acid and Mixed Salt Systems

| Ex | Asp (g) | H₂SO₄ (g)I | Additive (g)II | Additive (g)III K₂SO₄ | Mole Ratio Asp:I:II:III | Temp° C. Time h | Mw:Mn | % Pure | % Conversion |
|---|---|---|---|---|---|---|---|---|---|
| 7 | 30 | 58.68 | (NH₄)₂SO₄;95.56 | 25.82 | 1:2.59:3.23:0.66 | 185;1 | 3206;1604 | 97 | 89 |
| 8 | 30 | 73.46 | Na₂SO₄;52.24 | 58.79 | 1:3.24:1.5:1.73 | 185;2 | 3169;1778 | 97 | 81 |
| 9 | 30 | 75.68 | Na₂SO₄;52.24 | 58.79 | 1:3.24:1.5:1.73 | 200;2 | 4169;2105 | 97 | 81 |

As shown by the data in Table 2, the use of a sulfuric acid-mixed sulfate salt system employing two sulfate salts in the reaction medium produced polysuccinimide of relatively high purity with relatively high conversion. The MW of the produced polysuccinimide was in the range of about 3,100 and about 4,200.

EXAMPLE 11

Preparation of Polysuccinimide by Solution Polymerization of Aspartic Acid in a Sulfuric Acid-Mixed Sulfate System In Example 11, the general method employed in Examples 1–6 was followed, except that the preformed solvent mixture contained concentrated sulfuric acid (98% w/w, about 75.68 g, 0.742 mol), ammonium sulfate (99%, about 82.18 g, 0.616 mol) and potassium sulfate (99%, about 22.21 g, about 0.126 mol). In addition, the preselected reaction temperature was about 180° C. and was maintained for a preselected period of time of about 1 hour.

After the preselected reaction time periods had expired, the general procedure for isolating and characterizing the reaction product employed as described for Examples 1–4 was followed for Example 11.

Each one of the dried reaction products was a off-white powder that was confirmed by IR analysis as being polysuccinimide. The procedure of Example 11 produced polysuccinimide having a purity of about 96% and a MW of about 2,255 with conversion of about 40%.

We claim:

1. A solution polymerization process for the production of polysuccinimide comprising:
   (a) dissolving aspartic acid in a solvent comprising a sulfur oxygen acid and a sulfur oxygen acid salt;
   (b) maintaining the solvent at an elevated temperature above about 110° C. for a time period sufficient to produce a polysuccinimide; and
   (c) recovering the produced polysuccinimide from the reaction mixture.

2. The method of claim 1 wherein the reaction temperature is in the range of about 110° C. to about 320° C.

3. The method of claim 1 wherein the reaction temperature is in the range of about 130° C. to about 300° C.

4. The method of claim 1 wherein the reaction temperature is about 185° C.

5. The method of claim 1 wherein the solvent is formed by combining a sulfur oxygen acid with a sulfur oxygen acid salt and heating with stirring.

6. The method of claim 1 wherein the sulfur oxygen acid is selected from the group consisting of sulfuric acid, fuming sulfuric acid, sulfamic acid, polysulfuric acid, sulfonic acid and mixtures thereof.

7. The method of claim 1 wherein the sulfur oxygen acid salt is selected from the group consisting of an inorganic salt, an organic salt and mixtures thereof.

8. The method of claim 1 wherein the inorganic salt is selected from the group consisting of an alkali metal salt, an alkaline earth metal salt, a transition metal salt, and mixtures thereof.

9. The method of claim 1 wherein the organic salt is a sulfate salt selected from the group consisting of urea sulfate, pyridinium sulfate, pyridinium bisulfate, ammonium sulfate, and mixtures thereof.

10. The method of claim 1 wherein the organic salt is a quaternary ammonium sulfate.

11. The method of claim 1 wherein the organic salt is tetramethylammonium sulfate.

12. The method of claim 1 wherein a molar ratio of sulfur oxygen acid to sulfur oxygen acid salt in the solvent is in the range of about 1:1 to about 1:1.5.

13. The method of claim 1 wherein a molar ratio of sulfur oxygen acid-sulfur oxygen acid salt solution to aspartic acid is about 3:1.

14. The method of claim 1 wherein the aspartic acid is added to the solvent with heating and stirring in a reaction vessel.

15. The method of claim 1 wherein the reaction time is in the range of about 5 minutes to about 4 hours.

16. The method of claim 1 wherein the reaction time is about 1 to about 3 hours.

17. The method of claim 1 wherein an inert gas blanket is maintained over the reaction mixture.

18. The method of claim 1 wherein a nitrogen blanket is employed over the reaction mixture.

19. The method of claim 1 wherein the polysuccinimide is recovered by filtration and drying under reduced pressure.

20. The method of claim 1 wherein the solvent is a mixture of sulfuric acid and ammonium sulfate.

21. The method of claim 1 wherein the solvent is a mixture of sulfuric acid, sodium sulfate, and potassium sulfate.

22. The method of claim 1 wherein the solvent is a mixture of sulfuric acid, ammonium sulfate, and potassium sulfate.

* * * * *